US006532811B2

(12) United States Patent
Turner et al.

(10) Patent No.: US 6,532,811 B2
(45) Date of Patent: Mar. 18, 2003

(54) METHOD OF WEAR TESTING A TIRE

(75) Inventors: John L. Turner, Akron, OH (US); David O. Stalnaker, Hartville, OH (US)

(73) Assignee: Bridgestone/Firestone North American Tire, LLC, Nashville, TN (US)

( * ) Notice: Subject to any disclaimer, the term of this patent is extended or adjusted under 35 U.S.C. 154(b) by 101 days.

(21) Appl. No.: 09/770,884

(22) Filed: Jan. 26, 2001

(65) Prior Publication Data

US 2002/0134148 A1 Sep. 26, 2002

(51) Int. Cl.$^7$ .............................................. E01C 23/00
(52) U.S. Cl. ............................................... 73/146; 73/8
(58) Field of Search ................................. 73/146, 146.2, 73/146.3, 146.4, 146.5, 146.8, 7, 8, 9; 340/441, 442, 443, 444, 445, 446, 447, 448

(56) References Cited

U.S. PATENT DOCUMENTS

| | | |
|---|---|---|
| 3,563,088 A | 2/1971 | Sperberg |
| 4,160,378 A | 7/1979 | Himmler ...................... 73/146 |
| 5,065,618 A | 11/1991 | Hodges, Sr. et al. .......... 73/146 |
| 5,245,867 A | 9/1993 | Sube et al. .................... 73/146 |
| 5,440,923 A | 8/1995 | Arnberg et al. ............... 73/146 |
| 5,510,889 A | 4/1996 | Herr ........................... 356/5.1 |
| 5,557,552 A | 9/1996 | Naito et al. .................. 364/565 |
| 5,561,244 A | 10/1996 | Olesky et al. ................. 73/146 |
| 5,639,962 A | 6/1997 | Maloney ....................... 73/146 |
| 5,641,900 A | 6/1997 | Di Bernardo et al. ........ 73/146 |
| 5,657,227 A | 8/1997 | Freitag ................. 364/424.034 |
| 5,750,890 A | 5/1998 | Fricke et al. .................. 73/146 |
| 5,774,374 A | 6/1998 | Scott et al. .................. 364/561 |
| 5,877,414 A | 3/1999 | Rui et al. ...................... 73/146 |
| 5,880,362 A | 3/1999 | Tang et al. .................... 73/146 |

FOREIGN PATENT DOCUMENTS

| | | |
|---|---|---|
| EP | 0 880 019 A2 | 11/1998 |
| EP | 0 969 276 A2 | 1/2000 |
| EP | 0 955 534 A3 | 3/2000 |

*Primary Examiner*—Hezron Williams
*Assistant Examiner*—Andre Allen
(74) *Attorney, Agent, or Firm*—John M. Vasuta; Michael Sand

(57) ABSTRACT

A method for indoor wear testing tires includes the steps of characterizing a vehicle and a wear test course and combining the characterized data to create input data for an indoor wear test machine. The input data allows the indoor wear test machine to accurately simulate an outdoor wear test course for the characterized vehicle. The method allows multiple wear test courses to be used with a single characterized vehicle and allows a single wear test course to be used with multiple characterized vehicles. The method allows tires to be wear tested in relatively short time periods in the controlled environment of the indoor laboratory. In addition, the method is relatively easy to set up and perform.

20 Claims, 3 Drawing Sheets

METHOD OF WEAR TESTING A TIRE

BACKGROUND OF THE INVENTION

1. Technical Field

The present invention generally relates to methods of wear testing tires and, more particularly, to a method for defining a tire load history that is used in an indoor wear test. Specifically, the present invention relates to a method of defining a tire load history and using the tire load history to conduct an indoor wear test on the tire.

2. Background Information

Automobile and tire manufacturers desire wear testing to be performed on tires. Different methods of wear testing tires are known in the art. In one known method, the test tires are placed on a vehicle that will be frequently driven. The tires are measured after the vehicle is driven a selected number of miles. Another known test procedure is performed indoor on a wear test drum. A wear test drum provides a rotating surface that engages the tire to simulate a road surface. The wear test drum provides mechanisms for varying the force between the tire and the rotating surface. The velocity of the rotating surface may also be varied. The user may simulate actual public road driving conditions by varying these forces and the velocity. The problem in the prior art is that the user cannot easily determine what forces and velocities to use to simulate public road driving conditions for a specific vehicle.

For instance, one may wish to simulate tire wear with a specific tire on a specific vehicle over a daily commute that includes country road, highway, and city road driving conditions. The total length of the daily commute over a one year period may be 15,000 miles. The forces between the tire and the road constantly change through this commute and the person conducting the indoor wear test desires to accurately simulate these forces on the test tire with the indoor test drum.

One method of predicting the tire forces is to instrument a test car with wheel force transducers that are mounted as part of the wheel and rotate with the wheel/tire assembly while the vehicle is driven over a controlled test track. The vehicle is equipped with a data acquisition system that stores signals from the transducers. For instance, front and rear radial force, lateral force, drive/brake force, and tire velocities may be recorded. The angular position of each transducer must also be recorded because the transducers rotate with the tires. A problem with this measurement system is that the equipment is difficult to transport from test location to test location, the setup time is long, and the vehicle cannot be driven on public roads while equipped with the transducers. The data is thus only gathered on a test track that simulates public road driving conditions. The process of gathering the force histories for a given car with a given tire is expensive and often consumes weeks of time. The process must be repeated for different cars and for different tires. The art thus desires a faster and easier method of generating tire loading histories for indoor wear tests. The art also desires that the method for generating the tire loading histories result in more accurate load histories for the test machine.

SUMMARY OF THE INVENTION

The present invention provides a method for determining tire load histories for use with an indoor wear test machine. Sample tire forces are measured with a test system. The data from the test system is used to create formulas that relate the tire forces to the accelerations experienced by the vehicle. An instrumented vehicle driven over a wear test course records data about the vehicle while it is driven over the course. This data is used with the formulas to create the input forces for an indoor wear test machine.

The invention also provides a method of translating the data gathered from the outdoor test vehicle into tire load data that may be used to operate an indoor tire wear test drum to perform an indoor tire wear test.

DETAILED DESCRIPTION OF THE DRAWINGS

The method of the present invention is generally performed by first characterizing the vehicle for which the tire is being wear tested. The method also requires a wear test course to be measured with a vehicle. The invention combines the course measurements with the vehicle characterization to create a load history that is used to drive an indoor mechanical wear test machine to wear test the tire. The resulting wear test accurately reflects the wear on the tire if the tire had been used on the vehicle over the test course. The invention allows the wear test to occur indoors without the hassle of mechanical breakdowns over a much shorter time than in the past. In addition to the convenience and time advantages, the test courses may be used with any vehicle characterizations to allow different vehicles to be tested on a single course. In addition, different courses may be used with a single vehicle characterization to compare how a tire will perform with a vehicle on different courses. The uncontrolled effect of weather variability is also avoided.

1. Vehicle Characterization

The vehicle characterization step of this method measures the forces experienced by the tires of a vehicle under a variety of driving conditions. The vehicle characterization step is performed on the vehicle on which the tires are to be wear tested for. For instance, if the tire to be wear tested is going to be used on a specific passenger car, the specific passenger car—or a similar car—should be used during the vehicle characterization step.

Figure 1:
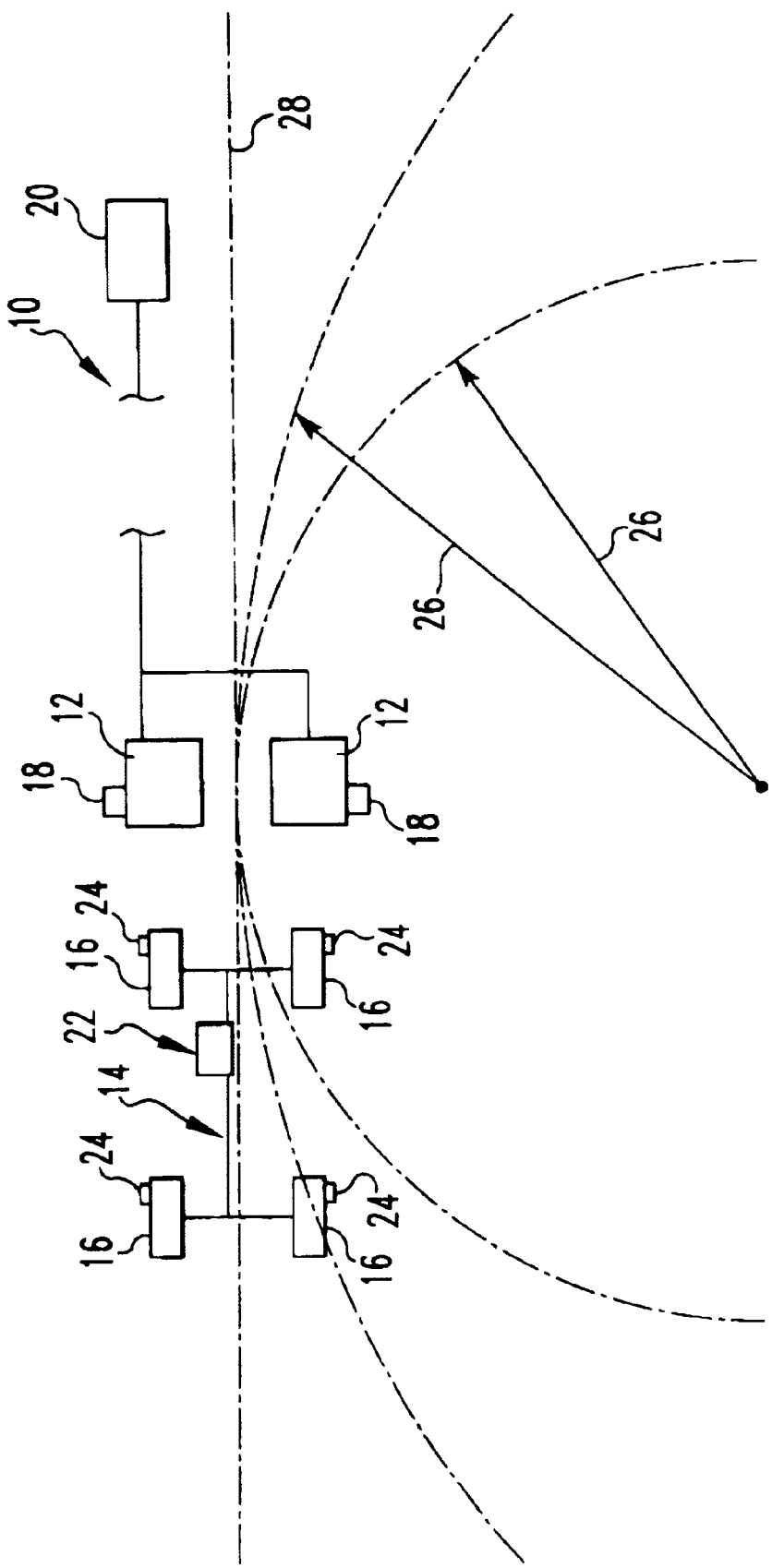
FIG. 1 is a schematic view of a dual force platform test facility.

The vehicle characterization step may be repeated for each type of vehicle for which a tire is to be wear tested. The vehicle characterization data may be gathered using a dual force platform measurement system 10 (FIG. 1). One system known in the art is referred to as AMTI Model OR6-5-2000. This system includes in-ground force platforms 12 configured to be driven over by the vehicle 14. The platform spacing is adjustable to accommodate different vehicle track widths. When the tires 16 of the vehicle 14 engage the force platforms 12, three directional forces (fore-aft (Fx), lateral (Fy), and vertical (Fz)) are measured by transducers 18 and recorded by an appropriate storage device 20 such as a computer. The data may be immediately stored by computer 20 or stored in an intermediate storage device and then stored in computer 20. Transducers 18 may be in communication with storage device 20 by wires or wireless transmissions. A measurement device may be used to measure the speed of vehicle 14. In another embodiment of the invention, the vehicle speed may be processed from the data gathered as tires 16 pass over platforms 12.

In addition to the directional force measurements, transducers 22 are positioned at the vehicle center of gravity to measure accelerations (fore-aft and lateral) during passage of tires 16 across force platforms 12. Appropriate wheel inclination measurement devices 24 are also used to measure the wheel inclination angles while tires 16 are passing over force platforms 12. One type of wheel inclination angle measurement device is disclosed in U.S. Pat. No. 5,561,244. Data from the two load platforms, the in-vehicle measurement of accelerations, and from the wheel inclination device are collected simultaneously.

The directional forces, velocity, accelerations, and wheel inclination angles are measured while vehicle 14 passes over platforms 12 at a range of speeds (for example, 2 to 20 miles per hour), turn radii 26 (for example, 30 feet to 200 feet), and straight driving acceleration/deceleration conditions 28 (for example, +0.5 g to −0.5 g). These test conditions span typically encountered levels of steering, cornering acceleration, braking acceleration, forward acceleration, and straight uniform motion produced in most day to day driving conditions on public roads and highways.

2. Course Characterization.

Figure 2:
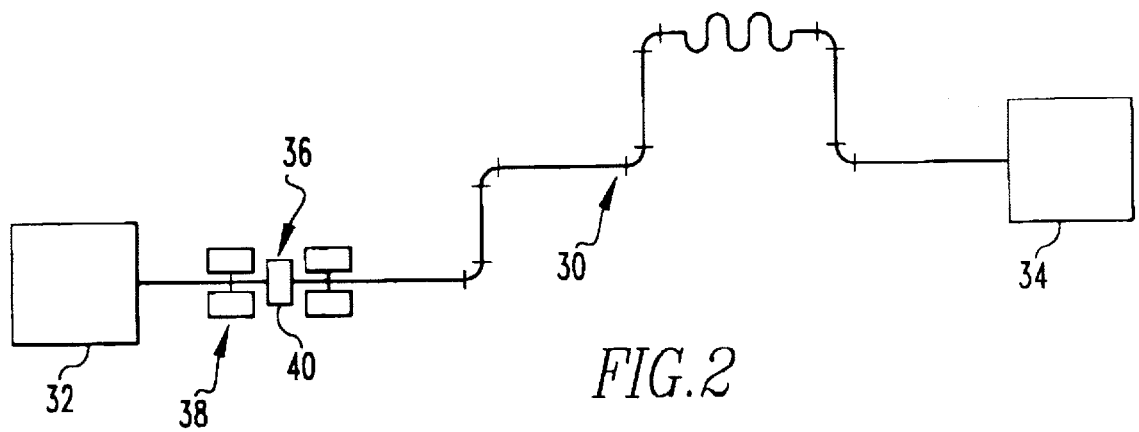
FIG. 2 is a schematic view of a wear test course being driven by a test vehicle.
Figure 3:
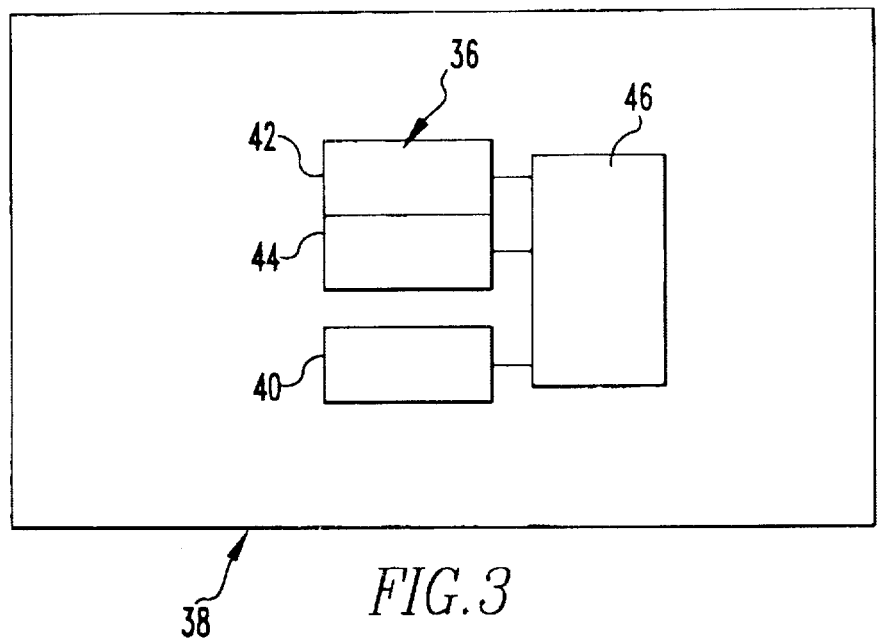
FIG. 3 is a schematic view of the instrumented vehicle depicted in FIG. 2.

Another step of the method of the present invention is to characterize a wear test course. A wear test course may be any test course of interest in which a tire manufacturer or automobile manufacturer is interested in gathering tire wear test information. For instance, the wear test course may be a typical commute for a target driver. In FIG. 2, a commuting wear course 30 includes a starting position at the driver's residence 32 and a final position at the driver's place of employment 34. The test course also may be a city driving course that would be typically used by a taxi cab driver. The type of wear test courses available to the method of the present invention are essentially limitless.

Test course 30 is characterized by installing a measuring device 36 in a vehicle 38 that measures fore-aft and lateral acceleration of the vehicle center of gravity while it is driven over course 30. An advantage is that test vehicle 38 does not have to be identical to test vehicle 14 described above. Another measurement device 40 records the velocity of the vehicle. Device 40 may be one that does not contact the road surface in order to determine velocity. Alternatively, device 40 measures the steering angle of vehicle 38 rather than the vehicle velocity. In one embodiment of the invention, two accelerometers 42 and 44 are used to measure the fore-aft acceleration and the lateral acceleration. An appropriate data storage device 46 such as a personal computer may be in communication with measurement devices 40, 42, and 44 to record test data at regular intervals while vehicle 38 is driven over test course 30. In one embodiment, the data is recorded every three feet of travel over the entire wear test course 30. One advantage of this step over prior methods is that the instrumentation required to gather this data may be placed inside the vehicle allowing the vehicle to remain "street legal" and driven over public roads. In the past, the instrumentation was on the outside of the vehicle. The present invention also prevents inclement weather from ruining the data gathering steps. Another advantage is that devices 40, 42, and 44 are compact and may be easily shipped. The measurements devices may also be quickly installed in the test vehicle.

The data gathered over the wear test course 30 is stored and creates a mathematical test course that can be applied to different vehicles. Each cornering maneuver, each braking and acceleration event, every hill and town captured and reproduced, in real-time, in this mathematical test course. The user may drive multiple test courses in order to create a library of test courses that may be applied to vehicles as desired.

3. Model Development.

After the user has characterized a vehicle, the user develops equations that relate the fore-aft (Fx), lateral (Fy), and vertical forces (Fz) to the fore-aft acceleration (Ax), lateral acceleration (Ay), and velocity (Vx) (or steering angle), measured on the wear test course. The user also develops an equation that relates the inclination angle (I.A.), of the tires to the forward acceleration, lateral acceleration, and velocity (or steering angle) measured on the wear test course. The equations are of the following generic functional form:

Fx=f1(Ax, Ay, Vx)
Fy=f2(Ax, Ay, Vx)
Fz=f3(Ax, Ay, Vx)
I.A.=f4(Ax, Ay, Vx)

Each of these equations includes coefficients that relate the accelerations and velocities to the forces. The values of the coefficients are determined by regression to give a best fit of the equation to the measured data. The equations and the coefficients constitute a vehicle model for predicting the forces and inclination angle when given the two accelerations and velocity. A separate set of equation coefficients is developed to characterize each wheel position on the vehicle. These equations are used to relate the wear test accelerations and velocities to the forces that are programmed into an indoor mechanical wear test machine.

The following table illustrates the terms used in each equation. The coefficients $a_0$ through $a_6$ are computed by least squares regression with the measured forces, inclination angles and accelerations from the vehicle characterization step. A shaded box indicates no use of that term in the equation for that independent variable. Checks, ✓, indicate that the term is included in the equation.

For example: $F_z = a_0 + a_1 * A_y + a_2 * A_y^2 + a_3 * K + a_4 * K^2 + a_5 * A_x$.

Figure 4:
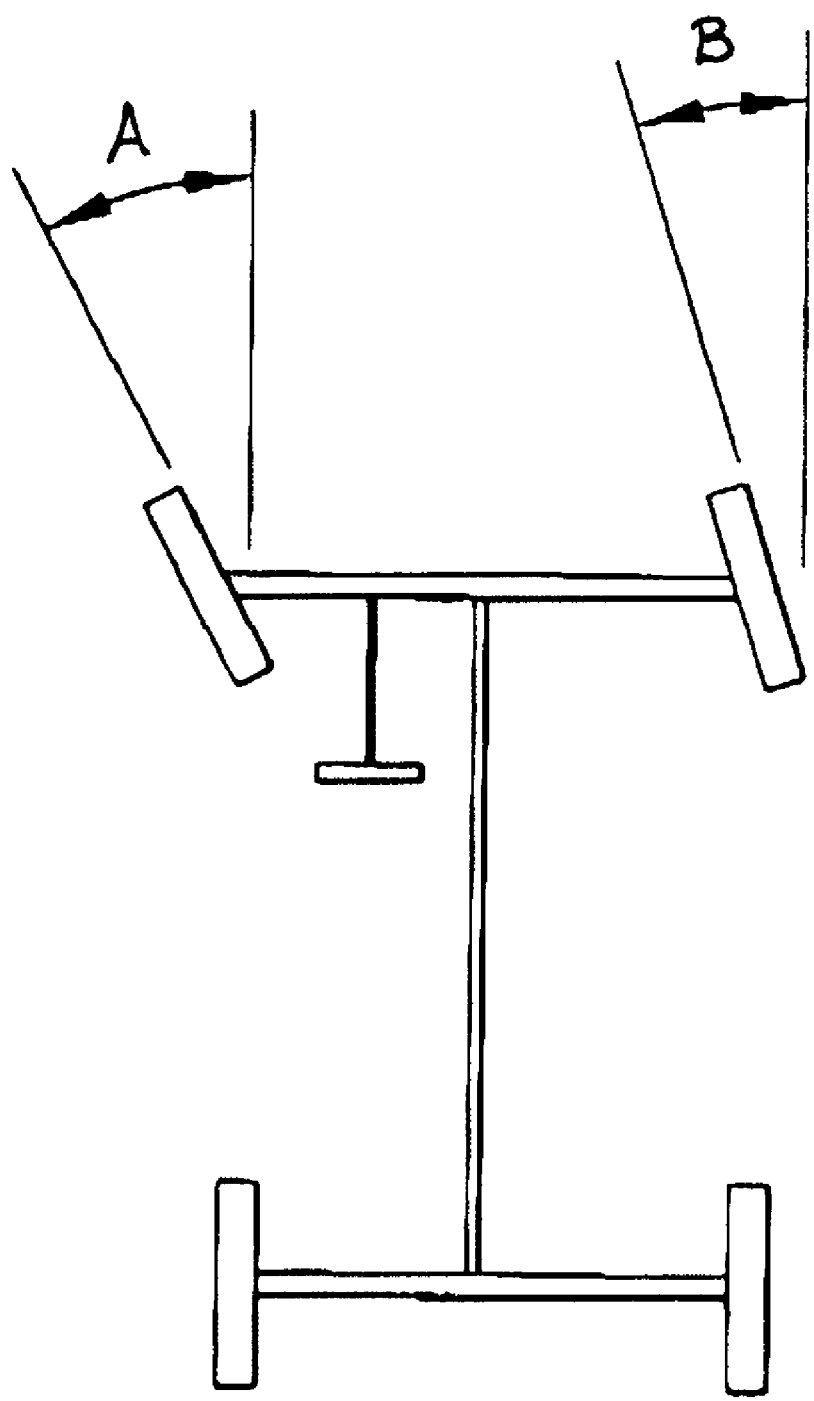
FIG. 4 is a schematic view of a vehicle showing the different steering angles of the front tires.

The variable K estimates road path curvature and is computed by $K = A_y / V_x^2$. The steering angle can be used in place of K if preferred. The acceleration terms are generally needed to capture load transfer due to inertial loads. The curvature terms are needed to account for forces produced by the geometric effects of the steering system. FIG. 4 shows why a vehicle steering system and vehicle geometry alters the angles of the tires with respect to the road surface. Angle A is different from angle B and thus the front tires experience different forces based on the radius of the curve.

TABLE OF EQUATIONS FOR VEHICLE LOAD TRANSFER CHARACTERIZATION

|  | $a_0$ | $a_1 * A_y$ | $a_2 * A_y^2$ | $a_3 * K$ | $a_4 * K^2$ | $a_5 * A_x$ | $a_6 * A_x^2$ |
|---|---|---|---|---|---|---|---|
| $F_z$ | ✓ | ✓ | ✓ | ✓ | ✓ | ✓ |  |
| $F_y$ | ✓ | ✓ | ✓ | ✓ | ✓ | ✓ |  |
| IA | ✓ | ✓ | ✓ | ✓ | ✓ | ✓ |  |
| $F_x$ | ✓ |  |  | ✓ | ✓ | ✓ | ✓ |

After the regressions are completed for Fx, one additional term, $a_7 * V_x^2$, is added to the Fx equation to help account for aerodynamic drag for tires on drive positions. The coefficient of this term is determined from the product of the aerodynamic drag coefficient and frontal area of the vehicle (determined from other sources). The contribution from this term is typically insignificant at the relatively low vehicle velocities used during the vehicle characterization process.

One additional modification is required if the indoor wear test machine (discussed in the next section) requires the spindle torque (My) as an input instead of Fx. In this case, an empirical, linear relationship between My and Fx is determined from a separate force and moment test machine for the tires under consideration and this relationship is used convert from Fx to My.

4. Indoor Mechanical Wear Test.

Once the equations relating the accelerations and velocities are known, the user may program an indoor mechanical wear test machine (such as the MTS Model 860 RoadWheel Tread Wear Test System) to simulate the outdoor wear test course. The user selects a characterized wear test course and calculates the forces as they relate to time for the vehicle. These forces are input into the indoor mechanical wear test machine and a number of miles is selected for the test. The indoor mechanical wear test machine rotates the tire against the drum and creates the forces input by the user. The wear test machine continuously repeats the wear test course as if the tire was being driven over the wear test course for the selected number of miles. For instance, the user may test the tire over a commuting course for 15,000 miles.

The method of the present invention allows tires to be efficiently and accurately wear tested using indoor testing equipment. The method allows the indoor testing equipment to effectively simulate each tire position of a particular vehicle traveling on a specific outdoor road wear course. The method allows the characterized vehicles to be tested on any characterized wear test course and allows a single wear test course to be used with any characterized vehicle.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of the invention is an example and the invention is not limited to the exact details shown or described.

What is claimed is:

1. A method of wear testing a tire comprising the steps of:
   (a) characterizing a vehicle;
   (b) characterizing a wear course;
   (c) predicting force data that represents the forces that would be experienced by the characterized vehicle if the vehicle were driven over the characterized wear course; and
   (d) using the force data to drive an indoor tire wear test machine.

2. The method of claim 1, wherein step (c) includes the step of relating the wear course characterization to the vehicle characterization.

3. The method of claim 2, wherein the step of relating the wear course characterization to the vehicle characterization includes the step of predicting the tire forces that would be experienced by a tire driven over the wear course by:
   (i) measuring the fore-aft and lateral accelerations experienced by a vehicle when the vehicle is driven over the wear course;
   (ii) measuring the velocities of the vehicle when the vehicle is driven over the wear course;
   (iii) measuring the three directional forces experienced by the tire during the vehicle characterization step;
   (iv) measuring the accelerations and velocities of the vehicle when the three directional forces are measured; and
   (v) creating formulas that relate the wear course accelerations and velocities to the three directional forces experienced by the tire.

4. The method of claim 3, wherein steps (i) and (ii) are performed by mounting measuring devices to a vehicle and driving the vehicle over the wear course.

5. The method of claim 4, further comprising the step of mounting the measuring devices inside the vehicle.

6. The method of claim 3, wherein step (iii) is performed by moving a tire mounted to a vehicle over a force platform.

7. A method of wear testing a tire comprising the steps of:
   (a) driving a first vehicle over a wear test course and recording accelerations and velocities experienced by the first vehicle while the vehicle is driven over the wear test course;
   (b) relating tire force measurements to the accelerations and velocity of a second vehicle; and
   (c) predicting the tire forces that would be created in the tires of a vehicle driven over the wear test course; and
   (d) inputting the predicted tire forces into an indoor tire wear test machine.

8. The method of claim 7, wherein step (a) includes the steps of measuring the fore-aft acceleration, lateral acceleration, and velocity of the first vehicle.

9. The method of claim 8, further comprising the step of recording measurements with instruments mounted on the vehicle.

10. The method of claim 9, further comprising the step of driving the first vehicle over a wear test course that includes public roads.

11. The method of claim 8, wherein step (b) includes the step of creating formulas that relate the accelerations and velocities to the three directional forces experienced by a tire.

12. The method of claim 11, wherein step (b) further includes the step of compensating at least one of the directional forces based on the turning radius of the vehicle.

13. A method of wear testing a tire comprising the steps of:
    (a) selecting a first test vehicle having at least a first test tire;
    (b) measuring the forces experienced by the at least first test tire while measuring the accelerations and velocity of the vehicle;
    (c) creating formulas that relate the forces experienced by the at least one test tire to the accelerations and velocity of the vehicle;
    (d) driving a second test vehicle over a wear test course and recording the velocity and accelerations of the vehicle as it is driven over the wear test course;
    (e) using the velocities and accelerations recorded over the wear test course to predict input forces for an indoor wear test machine;
    (f) inputting predicted the predicted input forces into the wear test machine; and
    (g) running an indoor wear test on a tire with the wear test machine using the input forces.

14. The method of claim 13, wherein step (b) includes measuring the wheel inclination angle of the at least first test tire while measuring the accelerations and velocity.

15. The method of claim 14, wherein step (c) includes the step of creating a formula that relates the wheel inclination angle to the accelerations and velocity of the vehicle.

16. The method of claim 13, wherein step (d) includes the step of measuring the fore-aft and lateral accelerations experienced by a vehicle when the vehicle is driven over the wear course.

17. The method of claim 13, wherein step (b) includes the step of measuring the three directional forces experienced by the at least first test tire.

18. A method of wear testing a tire; the method comprising the steps of:
   (a) characterizing a test vehicle without driving the test vehicle over a wear course;
   (b) characterizing a wear course without driving the test vehicle over the wear course;
   (c) predicting force data that represents the forces that would be experienced by the characterized vehicle if driven over the characterized wear course; and
   (d) using the force data to drive an indoor tire wear test machine.

19. The method of claim 18, wherein step (b) includes the step of recording accelerations and velocities experienced by the test vehicle while the test vehicle is driven over the wear course.

20. The method of claim 19, further comprising the step of recording the accelerations and velocities of the test vehicle with instruments mounted inside the vehicle.

* * * * *